(12) United States Patent
Lechner

(10) Patent No.: US 10,213,372 B2
(45) Date of Patent: *Feb. 26, 2019

(54) METHOD FOR SIMULTANEOUSLY AND PERMANENTLY RESHAPING AND COLORING KERATIN FIBERS

(71) Applicant: Henkel AG & Co. KGaA, Düsseldorf (DE)

(72) Inventor: Torsten Lechner, Düsseldorf (DE)

(73) Assignee: Henkel AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/487,898

(22) Filed: Apr. 14, 2017

(65) Prior Publication Data

US 2017/0252280 A1   Sep. 7, 2017

Related U.S. Application Data

(63) Continuation of application No. PCT/EP2015/070357, filed on Sep. 7, 2015.

(30) Foreign Application Priority Data

Oct. 15, 2014   (DE) .......................... 10 2014 220 921

(51) Int. Cl.

| | | |
|---|---|---|
| *A61K 8/46* | (2006.01) | |
| *A61Q 5/04* | (2006.01) | |
| *A61K 8/60* | (2006.01) | |
| *A61Q 5/10* | (2006.01) | |
| *A61K 8/81* | (2006.01) | |
| *A45D 7/04* | (2006.01) | |
| *A61K 8/04* | (2006.01) | |
| *A61K 8/19* | (2006.01) | |
| *A61K 8/22* | (2006.01) | |
| *A61K 8/23* | (2006.01) | |
| *A61K 8/24* | (2006.01) | |
| *A61K 8/34* | (2006.01) | |
| *A61K 8/41* | (2006.01) | |
| *A61K 8/44* | (2006.01) | |
| *A61K 8/49* | (2006.01) | |
| *A61K 8/55* | (2006.01) | |
| *A61K 8/67* | (2006.01) | |
| *A61K 8/86* | (2006.01) | |
| *A61K 8/92* | (2006.01) | |
| *A61K 8/96* | (2006.01) | |
| *A45D 2/00* | (2006.01) | |

(52) U.S. Cl.
CPC .................. *A61K 8/46* (2013.01); *A45D 7/04* (2013.01); *A61K 8/046* (2013.01); *A61K 8/19* (2013.01); *A61K 8/22* (2013.01); *A61K 8/23* (2013.01); *A61K 8/24* (2013.01); *A61K 8/345* (2013.01); *A61K 8/41* (2013.01); *A61K 8/415* (2013.01); *A61K 8/416* (2013.01); *A61K 8/44* (2013.01); *A61K 8/463* (2013.01); *A61K 8/4926* (2013.01); *A61K 8/55* (2013.01); *A61K 8/602* (2013.01); *A61K 8/676* (2013.01); *A61K 8/817* (2013.01); *A61K 8/8152* (2013.01); *A61K 8/86* (2013.01); *A61K 8/922* (2013.01); *A61K 8/96* (2013.01); *A61Q 5/04* (2013.01); *A61Q 5/10* (2013.01); *A45D 2/00* (2013.01); *A61K 2800/4324* (2013.01); *A61K 2800/596* (2013.01); *A61K 2800/87* (2013.01); *A61K 2800/884* (2013.01)

(58) Field of Classification Search
CPC ....................................................... A61Q 5/04
See application file for complete search history.

(56) References Cited

U.S. PATENT DOCUMENTS

| | | | |
|---|---|---|---|
| 4,630,621 A | | 12/1986 | Pontani |
| 5,161,553 A | * | 11/1992 | Cohen ...................... A61K 8/02 132/205 |
| 5,340,367 A | | 8/1994 | Schultz et al. |
| 2012/0285479 A1 | * | 11/2012 | Zirwen .................. A61K 8/046 132/208 |
| 2013/0081647 A1 | * | 4/2013 | Vohra ..................... A45D 34/00 132/221 |

FOREIGN PATENT DOCUMENTS

| | | | |
|---|---|---|---|
| DE | 19713698 C1 | 6/1998 | |
| EP | 0260716 A1 | 9/1987 | |
| EP | 0352375 A1 | 7/1988 | |
| EP | 1057470 A2 * | 12/2000 | ............. A61K 8/046 |
| EP | 1287812 A2 | 3/2003 | |

OTHER PUBLICATIONS

Google Patents Translation Brautigam (EP 1057470 A2, pub. Jun. 2000), accessed at https://patents.google.com/patent/EP1057470A2/en?q=A61Q5%2f04&g=mousse+foam&page=1 on Aug. 11, 2017.*

* cited by examiner

*Primary Examiner* — Susan T Tran
(74) *Attorney, Agent, or Firm* — P. Scott Smith

(57) ABSTRACT

Method for simultaneously and permanently reshaping and coloring keratin fibers, particularly human hairs, in a single process in which the keratinic fibers are first waved by way of a foam-type waving agent (M1) and then lightened or colored by way of a foam-type coloring agent (M2). The permanent wave is simultaneously fixed by the oxidizing agent included in the oxidative dyeing agent. The method according to the invention brings about a uniform waving and coloring result and causes little or no damage to the hair.

4 Claims, No Drawings

METHOD FOR SIMULTANEOUSLY AND PERMANENTLY RESHAPING AND COLORING KERATIN FIBERS

FIELD OF THE INVENTION

The present invention generally relates to a method for the permanently reshaping and changing the color of keratinic fibers, particularly human hairs, in a single process.

BACKGROUND OF THE INVENTION

The permanent styling of keratin-containing fibers is usually achieved by mechanically deforming the fibers and setting the style using suitable auxiliary means. Before and/or after this styling, the fibers are treated with a keratin-reducing preparation. After a rinsing process, the fibers are then treated in the so-called setting step with an oxidizing agent preparation and rinsed, and the styling aids (rollers, foam curlers) are removed after or during the setting step. If a mercaptan, e.g., ammonium thioglycolate, is used as a keratin-reducing component, then it cleaves a portion of the disulfide bridges of the keratin molecule into thiol groups, thus resulting in the softening of the keratin fibers and the swelling of the fibers under enlargement of the fiber diameter. During the subsequent oxidative setting, disulfide bridges are again linked in the hair keratin, thereby setting the keratin structure in the specified deformation. Alternatively, it is known to use sulfite instead of mercaptans for hair styling. By means of hydrogen sulfite solutions and/or sulfite solutions and/or disulfite solutions, disulfide bridges of the keratin are cleaved in a sulfitolysis process according to the equation

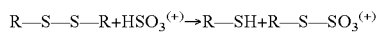

thus softening the keratin fibers. Hydrogen sulfite, sulfite, and disulfite-containing reducing agents do not have the strong intrinsic odor of the mercaptan-containing agents. As described above, the cleavage can be reversed in a setting step with the aid of an oxidizing agent under formation of new disulfide bridges.

If, in addition to the reshaping, a coloration of the keratinic fibers is also desired, the coloration can be performed as a separate treatment before or after reshaping. Particularly in the case of oxidative coloration, however, this results in extreme stressing of the keratinic fibers, since any oxidative treatment of the fibers damages their internal structure. What is more, such an approach is very time-consuming, since a time span of 2 or more weeks should be provided between the reshaping and the color treatment in order to avoid the aforementioned extreme stresses and associated damage. A number of methods for the simultaneous reshaping and coloring of keratinic fibers, particularly hairs, have therefore been proposed. In many cases, an oxidizing agent preparation is used for this purpose in the setting step which includes direct dyes and/or oxidation dye precursors in addition to the oxidizing agent. Such an approach is described, for example, in DE19713698 C1. However, this approach has the disadvantage that the coloration takes place at the same time as the setting—that is, it occurs at a point in time at which the fibers to be treated are subjected to the mechanical stress of the styling aids. This impedes the uniform application of the dyes, thus resulting in the danger of an uneven coloring result.

EP 0352375 A1 and EP 1287812 A2 disclose methods for simultaneously reshaping and coloring hairs in which a keratin-reducing preparation is used that already includes the necessary direct dyes and/or oxidation dye precursors. At least a portion of the respective keratin-reducing preparation is applied to the hair after it has been mechanically deformed. However, the direct dyes and/or oxidation dye precursors used for coloration do not always have satisfactory stability in comparison to the keratin-reducing preparation, so that when the direct dyes and/or oxidation dye precursors react with the keratin-reducing preparation, uneven reshaping and coloring results can occur.

It is therefore the object of the present invention to provide a method for reshaping and coloring keratinic fibers, particularly for human hairs, in which the reshaping and coloration can be performed in a single process and which yields a comparable or better reshaping result, colors the keratinic fibers uniformly in the desired color tone, and causes only slight or even absolutely no hair damage.

BRIEF SUMMARY OF THE INVENTION

A first object of the invention is therefore a method for permanently reshaping and changing the color of keratinic fibers, particularly human hairs, in a single process, with the method comprising the following method steps in the indicated sequence:
a) Styling of keratinic fibers using styling aids,
b) Application of an aqueous composition (M1) including at least one keratin-reducing compound, at least one alkalizing agent, and at least one surfactant from an applicator as a foam onto the keratinic fibers located on the styling aids and leaving this composition (M1) on the keratinic fibers located on the styling aids for a period of 5 to 50 minutes,
c) Rinsing and, optionally, drying of the keratinic fibers located on the styling aids,
d) Application of a composition (M2) including at least one oxidation dye precursor, at least one oxidizing agent, at least one alkalizing agent, and at least one surfactant from an applicator as a foam onto the keratinic fibers located on the styling aids and leaving this composition (M2) on the keratinic fibers located on the styling aids for a period of 10 to 15 minutes,
e) Removal of the styling aids from the keratinic fibers,
f) Distribution of the composition applied in step (d) to the keratinic fibers and/or repeated application of the composition (M2) including at least one oxidation dye precursor, at least one oxidizing agent, at least one alkalizing agent, and at least one surfactant from an applicator as a foam onto the keratinic fibers and leaving this composition (M2) on the keratinic fibers located on the styling aids for a period of 15 to 30 minutes,
g) Rinsing of the keratinic fibers, and
h) Optionally, application of a post-treatment agent to the keratinic fibers.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Surprisingly, it was found that the object is achieved by a method in which the keratinic fibers, after application onto styling aids, are styled by means of a reducing agent composition, followed by application of an oxidative dyeing composition. Through the removal of the styling aids during the exposure time of the oxidative dyeing composition, both an outstanding reshaping result and even an intensive coloration and/or lightening are achieved. In addition, the use of the method according to the invention surprisingly results in little or even absolutely no hair damage. The consecutive execution of the reshaping and coloration step enables significant time-savings to be achieved compared to reshaping and coloration performed separately and sequentially in two processes.

All animal hairs, e.g., wool, horse hair, angora hair, pelts, feathers, and products or textiles produced from same, can be used as keratin-containing fibers. Preferably, however, the invention is used in the context of a simultaneous shaping and coloring of the hair, particularly permanent waving and coloring of smooth hairs and wigs.

According to the invention, the permanent styling and color-changing, i.e., the permanent wave and oxidative hair coloration, is performed in a single process. Here, "in a single process" means that 30 seconds to 2 hours, preferably 30 seconds to 1 hour, more preferably 30 seconds to 30 minutes, particularly 30 seconds to 15 minutes, lie between the end of one method step and the beginning of the next.

In terms of the method according to the invention, styling aids are so-called perm curlers or foam curlers.

Methods that are especially preferred result in a waving of the keratinic fibers with simultaneous lightening or changing of the hair color that was present before the method according to the invention is carried out. It is therefore preferred that a permanent wave be performed as a permanent reshaping and lightening or coloration be performed as a color change.

In the first method step (method step (a)) of the method according to the invention, the keratinic fibers are styled using styling aids. Perm curlers or foam curlers in particular are suitable in this context as styling aids. In order to facilitate the application of the keratinic fibers onto the styling aids, it can be preferred according to the invention if the keratin-containing fibers are moistened with water before method step (a) or washed with a hair-cleansing composition. The use of a hair-cleansing composition, particularly a hair shampoo, can be expedient if the hair is very dirty. After the hair shampoo has been rinsed out, the hair is rubbed down with a hand towel in such a way that palpable residual moisture remains in the hair. If the hair is not very dirty, it is preferred that the keratinic fibers be moistened with water in order to ensure separation into defined, individual hair strands. This can be achieved, for example, by spraying the fibers with a liquid, preferably with water.

In order to prevent pronounced stressing and damaging of the keratinic fibers during the method according to the invention, styling aids are preferably used in method step (a) which have a certain diameter. Especially preferred methods according to the invention are therefore characterized in that the styling aids used in method step (a) have a diameter from 1 to 10 cm, preferably from 1 to 8 cm, more preferably from 1 to 6 cm, particularly from 2 to 5 cm.

Through the use of styling aids having holes, both the reshaping and the oxidative coloring result, particularly the lightening or coloration, can be improved, since the even wetting of the keratinic fibers located on the styling aids with the reshaping and coloring agent is enabled in this way. It is therefore preferred according to the invention if the styling aids used in method step (a) have holes in a number from 1 to 10,000, preferably from 10 to 9,000, more preferably from 100 to 8,000, even more preferably from 300 to 7,000, and particularly from 500 to 6,000.

In a second method step (method step (b)), an aqueous composition (M1) is applied to the keratinic fibers, which are already located on the styling aids. This aqueous composition (M1), which is referred to hereinafter as a reducing agent, is left on the keratinic fibers for a period of 5 to 50 minutes.

Exposure times of the reducing agent that are rather shorter are preferred according to the invention, however. Especially preferred methods according to the invention are therefore characterized in that the composition (M1) used in method step (b) is left on the keratinic fibers located on the styling aids for a period of 10 to 50 minutes, preferably 10 to 45 minutes, particularly 20 to 40 minutes. Using a reducing agent (M1) has the effect that a portion of the disulfide bridges of the keratin molecule is reduced to thiol groups, thereby softening the keratin fibers on the styling aids. In order to achieve a uniform reshaping result, particularly permanent wave result, the reducing agent (M1) should be applied uniformly onto the keratinic fibers. For this purpose, it can be preferred to repeat the application of the reducing agent multiple times in order to ensure that the keratinic fibers are wetted completely with the reducing agent (M1).

After the exposure time of the reducing agent, the keratinic fibers on the styling aids are rinsed out and optionally dried (method step (c)). The hair can be dried using a hand towel or handheld hairdryer or hooded hairdryer. When drying with a hand towel, a palpable residual moisture remains in the fibers. When drying with a handheld hairdryer or hooded hairdryer, the moisture content of the dry fibers is substantially in equilibrium with the humidity of the air, or the fibers are able to take up moisture from the surrounding air. It is preferred according to the invention that drying be performed, however, since better lightening and coloring results are achieved in that case.

After drying of the keratinic fibers, a composition (M2), hereinafter also referred to as a dyeing agent, is applied in method step (d) of the method according to the invention to the keratinic fibers still located on the styling aids and left to act for a period of 10 to 15 minutes. In order to ensure a uniform and complete wetting of the keratinic fibers, it can be preferred for dyeing agents to be applied multiple times in succession to the keratinic fibers. For one, the oxidizing agent present in the dyeing agent, particularly hydrogen peroxide, results in the oxidation of the thiol groups of the softened keratinic fibers and thus to the setting of the reshaped, particularly waved, keratinic fibers. For another, the oxidizing agent in the composition (M2) results in the formation of the desired color from the oxidation dye precursors, particularly to the lightening or coloration of the keratinic fibers.

After removal of the styling aids in method step (e), the dyeing agent remaining on the keratinic fibers is distributed and/or dyeing agent is applied again in order to achieve a maximally complete wetting of all of the keratinic fibers and thus outstanding setting and lightening or coloring performance (method step (f) and left to act for a period of 15 to 30 minutes. However, exposure times that are rather shorter are preferred according to the invention. Methods according to the invention are therefore characterized in that the composition (M2) used in method step (f) is left on the keratinic fibers for a period of 15 to 25 minutes, particularly 15 to 20 minutes.

After the rinsing-out of the composition (M2) in step (g) of the method according to the invention, a reshaping, particularly waving, as well as a color change, particularly lightening or coloration, of the keratinic fibers is achieved without the need to carry out an additional oxidative coloring process and without unduly damaging the keratinic fibers through the simultaneous waving and lightening or coloration. Enormous time-savings are thus achieved in comparison to the carrying out of the waving and lightening or coloration as two separate processes, since a period of 1 to 3 weeks can usually pass between these processes in order to prevent hair damage. In the context of the method according to the invention, it is preferred if water with a temperature of 20 to 45° C. is used for the rinsing of the keratinic fibers performed in method step (g).

The aqueous composition (M1) used in method step (b) is a reducing agent that includes at least one keratin-reducing compound. According to the invention, an aqueous composition is understood as being a composition that includes at least 50 wt % water with respect to the total weight of the composition. This aqueous composition (M1) can be present in various forms, for example as a lotion, as an oil-in-water emulsion, or as a water-in-oil emulsion. It is preferred according to the invention if the composition (M1) used in method step (b) includes, as a keratin-reducing compound, at least one compound from the group of thioglycolic acid, thiolactic acid, thiomalic acid, phenylthioglycolic acid, mercaptoethanesulfonic acid as well as the salts and esters thereof, cysteamine, cysteine, Bunte salts and salts of sulfurous acid, alkali disulfites, such as sodium disulfite ($Na_2S_2O_5$) and potassium disulfite ($K_2S_2O_5$), for example, as well as magnesium disulfite and ammonium disulfite (($NH_4)_2S_2O_5$), hydrogen sulfites as alkali, magnesium, ammonium or alkanolammonium salts based on a $C_2$-$C_4$ mono-, di- or trialkanolamine, as well as sulfites as alkali, ammonium or alkanolammonium salts based on a $C_2$-$C_4$ mono-, di- or trialkanolamine. The abovementioned compounds are capable of reducing the disulfide bridges of the keratin to thiol groups, thus ensuring the softening of the keratin fibers that is necessary for the reshaping.

It has proven to be especially advantageous in the context of this embodiment if the composition (M1) used in method step (b) includes, as a keratin-reducing compound, at least one compound from the group of thioglycolic acid, thiolactic acid, cysteine, and salts thereof. The use of the abovementioned keratin-reducing compounds ensures sufficient reduction of the disulfide bridges at relatively low concentrations, so the development of unpleasant odors during reshaping can be largely avoided.

It is preferred according to the invention if the composition (M1) used in method step (b) includes at least one keratin-reducing compound in a total quantity of 5 to 20 wt %, preferably 7 to 18 wt %, more preferably 9 to 16 wt %, and particularly 10 to 15 wt % with respect to the total weight of the aqueous composition (M1). The use of such quantities ensures sufficient softening of the keratin fibers without unduly damaging the fibers or releasing unpleasant odors during use. As a result, a good reshaping result can be achieved without undue hair damage.

The reducing agents (M1) used in method step (b) also include at least one alkalizing agent in order to set the desired pH value and support the swelling of the hair or enlargement of the hair diameter. Preferably, the composition (M1) used in method step (b) includes, as an alkalizing agent, at least one compound from the group of sodium hydroxide, potassium hydroxide, ammonium hydroxide, ammoniac, monoethanolamine, 2-amino-2-methyl propane, and alkali and ammonium hydrogen carbonates. These alkalizing agents are stable even in the presence of the reducing compound(s) and do not result in instabilities and pH fluctuations in the reducing agents (M1).

In this context, it is advantageous if the composition (M1) used in method step (b) includes ammonium hydrogen carbonate and/or ammonium hydroxide as an alkalizing agent. The use of these alkalizing agents has proven to be especially advantageous in terms of the pH stability and storage stability of the reducing agents (M1).

According to one embodiment of the present invention, the composition (M1) used in method step (b) includes the at least one alkalizing agent in a total quantity of 0.1 to 15 wt %, preferably 0.5 to 12 wt %, more preferably 1.0 to 10 wt %, and particularly 1.5 to 7 wt % with respect to the total weight of the aqueous composition (M1). The use of the abovementioned quantities results in outstanding supporting of the hair swelling. Moreover, the setting of the desired pH values from pH 5 to pH 12 is ensured when using these quantities.

Compositions that are preferably used in method step (b) in the context of the present invention therefore have a pH from 5 to 12, preferably from 5 to 10, and particularly from 5 to 9.5, at 20° C.

Especially good results are obtained in the context of the present invention if the composition (M1) used in method step (b) has a weight ratio of the keratin-reducing compound to the alkalizing agent from 1:200 to 1:1, preferably from 1:50 to 1:1, more preferably from 1:30 to 1:1, even more preferably from 1:20 to 1:1, and particularly from 1:10 to 1:1. The use of the abovementioned weight ratios results in especially effective softening and/or swelling of the hair and thus ensures a long-lasting reshaping result that is not even significantly influenced, particularly not significantly worsened, by the subsequent coloring or lightening step.

In order to achieve better wetting of the keratinic fibers with the reducing agent (M1), the composition (M1) used in method step (b) includes, as a surfactant, at least one compound from the group of alkyl (ether) sulfates, alkyl betaines, and nonionic surfactants. In terms of the present invention, surfactants are amphiphilic (bifunctional) compounds that consists of at least one hydrophobic and at least one hydrophilic moiety. The use of surfactant(s) in the reducing agents (M1) ensures clean and locally restricted application and enables uniform and rapid application to the keratinic fibers. Furthermore, running or flowing-out of the reducing agent (M1) from the keratinic fibers during the exposure time is also prevented.

In the framework of this embodiment, the composition (M1) used in method step (b) includes, as surfactant, alkyl (ether) sulfates of formula (I)

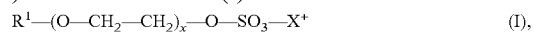

$$R^1—(O—CH_2—CH_2)_x—O—SO_3—X^+ \qquad (I),$$

where $R^1$ stands for a linear or branched, saturated or unsaturated alkyl group with 8 to 30 carbon atoms, x stands for the number 0 or for numbers from 1 to 12, and $X^+$ stands for an alkali metal ion or ammonium ion. Preferred alkyl (ether) sulfates are selected from the group of straight-chain or branched alkyl (ether) sulfates with an alkyl residue with 8 to 18, particularly with 10 to 16 carbon atoms and 0 or 1 to 6 ethylene oxide units, preferably sodium lauryl sulfate and/or sodium laureth sulfate.

Furthermore, it is advantageous in the framework of this embodiment if the composition (M1) used in method step (b) includes, as surfactant, alkyl betaines of formula (II)

where $R^1$ and $R^3$, each independently of one another, stand for a $C_1$-$C_4$ alkyl group or a $C_2$-$C_4$ hydroxyalkyl group and for $R^2$ stands for a saturated or unsaturated $C_{10}$-$C_{20}$ alkyl chain. One especially preferred alkyl betaine of formula (II) is coco alkyldimethyl betaine, for example, which is commercially available under the trade name Genagen KB from Clariant.

Moreover, a provision can be made in the context of this embodiment that the composition (M1) used in method step (b) includes, as surfactant, ethoxylated and/or propoxylated alcohols and carboxylic acids with 8 to 13 carbon atoms and 2 to 30 ethylene oxide and/or propylene oxide units, addition products of 5 to 60 mol ethylene oxide to castor oil and hardened castor oil, alkyl polyglucosides of the formula $R^1O$-$[G]_p$, in which $R^1$ stands for an alkyl and/or alkenyl residue with 4 to 22 carbon atoms, G stands for a sugar residue with 5 or 6 carbon atoms, and p stands for numbers from 1 to 10, monoethanolamides of carboxylic acids with 8 to 30 carbon atoms, as well as mixtures thereof. In the formula $R^1O$-$[G]p$, the index number p indicates the degree of oligomerization (DP), i.e., the distribution of mono- and oligoglucosides, and stands for a number between 1 and 10. While p can be an integer in a given compound and can assume above all the values p=1 to 6 here, the value p is an analytically determined quantity identified for a specific alkyl oligoglucoside and usually represents a fractional number. Alkyl and/or alkenyl oligoglucosides having a mean degree of oligomerization p from 1.1 to 3.0 are preferably used according to the invention. From an application engineering perspective, such alkyl and/or alkenyl oligoglucosides are preferred whose degree of oligomerization is less than 1.7 and particularly lies between 1.2 and 1.7. The alkyl or alkenyl residue $R^1$ can be derived from primary alcohols with 4 to 6, preferably 8 to 16 carbon atoms. Alkyl oligoglucosides based on hardened $C_{12/14}$ coco alcohol with a DP from 1-3, such as those which are commercially available under the INCI designation "coco glucoside," for example, are very especially preferred according to the invention. Moreover, suitable nonionic surfactants are, for example, addition products of 20 to 60 mol ethylene oxide to castor oil and hardened castor oil, particularly the compounds known by the INCI designations PEG-40 Hydrogenated Castor Oil and PEG-60 Hydrogenated Castor Oil.

The use of the abovementioned surfactants in the reducing agent (M1) results in a mousse-type composition that can be applied easily and rapidly and ensures outstanding wetting of the keratinic fibers on the styling aids. A mousse-type composition is understood according to the invention as a composition that is present as a foam. Foams are colloid-chemical systems composed of gas-filled cells that are bordered by fluid, semifluid, or highly viscous cell webs.

In order to obtain a sufficient quantity of foam, the previously mentioned surfactants can be used in certain quantity ranges. Methods that are preferred according to the invention are therefore characterized in that the composition (M1) used in method step (b) includes the at least one surfactant in a total quantity of 1.0 to 20 wt %, preferably 2.0 to 15 wt %, more preferably 2.5 to 10 wt %, and particularly 3.0 to 7.0 wt % with respect to the total weight of the aqueous composition (M1). The use of the abovementioned quantities of surfactant ensures outstanding wetting of the keratinic fibers and results in aqueous compositions (M1) that can be applied cleanly and rapidly due to their mousse-type consistency. Moreover, this consistency prevents the reducing agent composition (M1) from dripping out during the exposure time.

The reducing agents (M1) used in relation to the method according to the invention can be packaged as a propellant-free composition or as a propellant-containing composition. Propellant-free reducing agents (M1) can be delivered in any propellant gas-free spray system having a dispensing container and a spray valve—for example, in a flexible pressure bottle with a dip tube and spray valve (squeeze bottle) or in a pump spray bottle whose pump lever is actuated with the index finger or with the entire hand in the manner of a trigger.

If the reducing agents (M1) are packaged as a propellant-containing composition, they additionally include at least one propellant. In the context of this embodiment, the aqueous composition (M1) includes at least one propellant selected from the group of $N_2O$, dimethyl ether, $CO_2$, air, propane, n-butane, iso-butane, n-pentane, iso-pentane, as well as mixtures thereof, preferably a mixture of propane and n-butane in a weight ratio of 15:85.

In the context of this embodiment, it is also preferred if the aqueous composition (M1) includes the at least one propellant in a total quantity of 0.5 to 16 wt %, preferably 1.0 to 14 wt %, more preferably 3.0 to 13 wt %, even more preferably 4.0 to 12 wt %, particularly 5.5 to 10 wt % with respect to the total weight of the composition (M1).

The composition (M2) used in method step (d) is an oxidative hair dye, particularly a dyeing agent that lightens or changes the color of the hair before the method according to the invention is carried out. It is therefore preferred if the composition (M2) used in method step (d) includes at least one oxidation dye precursor in the form of a developer component and at least one oxidation dye precursor in the form of a coupler component. Especially good coloring results are obtained when using oxidation dye precursor of the developer type and of the coupler type in the dyeing agents (M2).

The developer and coupler components are usually used in free form. In the case of substances with amino groups, however, it can be preferred to use their salt form, particularly in the form of the hydrochlorides and hydrobromides or sulfates.

Compositions (M2) are preferred according to the invention which include developer and coupler components in respective total quantities of 0.001 to 10 wt %, preferably 0.01 to 8 wt %, more preferably 0.1 to 5 wt %, and particularly 0.5 to 3 wt % with respect to the total weight of the composition (M2).

In another preferred embodiment, the method according to the invention is therefore characterized in that the composition (M2) used in method step (b) includes the at least one oxidation dye precursor a total quantity of 0.001 to 10 wt %, preferably 0.01 to 8 wt %, more preferably 0.1 to 5 wt %, and particularly 0.5 to 3 wt % with respect to the total weight of the composition (M2).

Suitable oxidation dye precursors of the developer type are p-phenylenediamine and derivatives thereof, for example. Preferred p-phenylenediamines are selected from among one or more of the compounds of the group consisting of p-phenylenediamine, p-toluylenediamine, 2-chloro-p-phenylenediamine, 2,3-dimethyl-p-phenylenediamine, 2,6-dimethyl-p-phenylenediamine, N,N-bis-(2-hydroxyethyl)-p-phenylenediamine, 2-(2-hydroxyethyl)-p-phenylenediamine, 2-(1,2-dihydroxyethyl)-p-phenylenediamine, N-(2-hydroxypropyl)-p-phenylenediamine, N-(4'-aminophenyl)-p-phenylenediamine, 2-methoxymethyl-p-phenylenediamine, N-phenyl-p-phenylenediamine, 2-(2-hydroxyethyloxy)-p-phenylenediamine and N-(4-amino-3- methyl-phenyl)-N-[3-(1H-imidazole-1-yl)propyl]amine, as well as physiologically acceptable salts thereof.

It may also be preferred according to the invention to use compounds as developer components which include at least two aromatic nuclei that are substituted with amino and/or hydroxyl groups. Preferred binuclear developer components are selected from among N,N'-bis-(2-hydroxyethyl)-N,N'-bis-(4'-aminophenyl)-1,3-diaminopropane-2-ol, N,N'-bis-(4-aminophenyl)-1,4-diazacycloheptane, bis-(2-hydroxy-5-aminophenyl)methane, as well as physiologically acceptable salts thereof.

Moreover, it may be preferred according to the invention to use a p-aminophenol derivative or one or the physiologically acceptable salts thereof as a developer component. Preferred p-aminophenols are p-aminophenol, N-methyl-p-aminophenol, 4-amino-3-methylphenol, 4-amino-2-aminomethyl-phenol, 4-amino-2-(1,2-dihydroxyethyl)-phenol, 4-amino-2-(diethylaminomethyl)phenol, as well as physiologically acceptable salts thereof.

Furthermore, the developer component can be selected from among o-aminophenol and derivatives thereof, preferably from 2-amino-4-methylphenol, 2-amino-5-methylphenol, 2-amino-4-chlorophenol and/or physiologically acceptable salts thereof.

Moreover, the developer component can be selected from among heterocyclic developer components such as pyrimidine derivatives, pyrazole derivatives, pyrazolopyrimidine derivatives, or physiologically acceptable salts thereof. Preferred pyrimidine derivatives are 2,4,5,6-tetraaminopyrimidine, 4-hydroxy-2,5,6-triaminopyrimidine, and physiologically acceptable salts thereof. One preferred pyrazole derivative is 4,5-diamino-1-(2-hydroxyethyl)pyrazole as well as physiologically acceptable salts thereof. Pyrazolo[1,5-a]pyrimidines are particularly preferred as pyrazolopyrimidines.

Preferred oxidation dye precursors of the developer type are therefore selected from the group consisting of p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-Amino-3-methylphenyl)-N-[3-(1H-imidazole-1-yl)propyl]amine, N,N'-bis-(2-hydroxyethyl)-N,N'-bis-(4-aminophenyl)-1,3-diamino-propane-2-ol, bis-(2-hydroxy-5-aminophenyl)methane, 1,3-Bis-(2,5-diaminophenoxy)-propane-2-ol, N,N'-bis-(4-aminophenyl)-1,4-diazacycloheptane, 1-bis-(2,5-diaminophenyl)-1,4,7-tetraoxadecane, 4-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazol, 2,4,5,6-tetraaminopyrimidine, 4-hydroxy-2,5,6-triaminopyrimidine, 2-hydroxy-4,5,6-triaminopyrimidine, or the physiologically acceptable salts of these compounds.

Especially preferred developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazole-1-yl)propyl]amine and/or 4,5-diamino-1-(2-hydroxyethyl)-pyrazole as well as physiologically acceptable salts thereof.

In addition to at least one developer component, the composition (M2) used in method step (d) additionally includes at least one coupler component as an oxidation dye precursor. m-phenylenediamine derivatives, naphthols, resorcinol and resorcinol derivatives, pyrazolone, and m-aminophenol derivatives are generally used as coupler components.

Coupler components that are preferred according to the invention are selected from among a) m-aminophenol and derivatives thereof, particularly 3-aminophenol, 5-amino-2-methylphenol, 3-amino-2-chloro-6-methylphenol, 5-amino-4-chloro-2-methylphenol, 5-(2'-hydroxyethyl)-amino-2-methylphenol, and 2,4-dichloro-3-aminophenol, b) o-aminophenol and derivatives thereof, such as 2-amino-5-ethylphenol, c) m-diaminobenzene and derivatives thereof, such as, for example, 2,4-diaminophenoxyethanol, 1,3-bis-(2',4'-diaminophenoxy)-propane, 1-methoxy-2-amino-4-(2'-hydroxyethylamino)benzene, 2,6-bis-(2'-hydroxyethylamino)-1-methylbenzene, 2-({3-[(2-hydroxyethyl)amino]-4-methoxy-5-methylphenyl}amino)ethanol, and 2-({3-[(2-hydroxyethyl)amino]-2-methoxy-5-methylphenyl}-amino)ethanol, d) o-diaminobenzene and derivatives thereof, e) di- and trihydroxybenzene derivatives, particularly resorcinol, 2-chlororesorcinol, 4-chlororesorcinol, 2-methylresorcinol, and 1,2,4-trihydroxybenzene, f) pyridine derivatives, particularly 3-amino-2-methylamino-6-methoxypyridine, 2,6-diaminopyridine, 2,6-dihydroxy-3,4-dimethylpyridine, 2-amino-3-hydroxypyridine, and 3,5-diamino-2,6-dimethoxypyridine, g) naphthaline derivatives, such as 1-naphthol and 2-methyl-1-naphthol, h) morpholine derivatives, such as 6-hydroxybenzomorpholine, i) quinoxaline derivatives, j) pyrazole derivatives, such as 1-phenyl-3-methylpyrazole-5-on, k) indole derivatives, such as 6-hydroxyindole, l) pyrimidine derivatives, or m) methylenedioxybenzene derivatives, such as 1-(2'-hydroxyethyl)-amino-3,4-methylenedioxybenzene as well as physiologically acceptable salts thereof.

Coupler components that are preferred according to the invention are therefore selected from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-Bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholine-4-yl-phenyl)amino]ethanol, 3-amino-4-(2-methoxyethoxy)-5-methylphenylamine, 1-amino-3-bis-(2-hydroxyethyl)aminobenzene, resorcin, 2-methylresorcin, 4-chlororesorcin, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-on, 1-naphthol, 1,5-dihydroxynaphthalene, 2,7-dihydroxynaphthalene, 1,7-dihydroxynaphthalene, 1,8-dihydroxynaphthalene, 4-hydroxyindol, 6-hydroxyindol, 7-hydroxyindol, 4-hydroxyindoline, 6-hydroxyindoline and/or 7-hydroxyindoline or the physiologically acceptable salts of the abovementioned compounds.

Coupler components that are especially preferred according to the invention are resorcinol, 2-methylresorcinol, 5-amino-2-methylphenol, 3-aminophenol, 2-(2,4-diamino-phenoxy)ethanol, 1,3-bis-(2,4-diamino-phenoxy)propane, 1-methoxy-2-amino-4-(2'-hydroxyethylamino)benzene, 2-amino-3-hydroxypyridine, 2,6-dihydroxy-3,4-dimethylpyridine, 1,5-dihydroxynaphthaline, 2,7-dihydroxynaphthaline and 1-naphthol as well as physiologically acceptable salts thereof.

In another embodiment, the method according to the invention is characterized in that the composition (M2) used in method step (d) includes, as an oxidation dye precursor, at least one developer and coupler component from the group consisting of p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1 h-imidazole-1-yl)propyl]amine, N,N-bis-(2-hydroxyethyl)-N,N-bis-(4-aminophenyl)-1,3-diamino-propane-2-ol, bis-(2-hydroxy-5-aminophenyl)methane, 1,3-bis-(2,5-diamino-phenoxy)-propane-2-ol, N,N'-bis-(4-aminophenyl)-1,4-diazacycloheptane, 1,10-bis-(2, 5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4, 5,6-triaminopyrimidine or the physiologically acceptable salts of these compounds, as well as, in addition, at least one coupler component from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)-propane, 1-methoxy-2-amino-4-(2-hydroxyethylamino)benzene, 1,3-bis(2,4-diaminophenyl)-propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methyl-phenyl}amino) ethanol, 2-({3-[(2-hydroxyethyl)amino]-4, 5-dimethylphenyl}amino)ethanol, 2-[3-morpholine-4-yl-phenyl)amino]-ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-di-hydroxy-3,4-dimethylpyridine, 3,5-diamino-2,6-dimethoxypyridine, 1-phenyl-3-methylpyrazole-5-on, 1-naphthol, 1,5-dihydroxynaphthaline, 2, 7-dihydroxynaphthaline, 1,7-dihydroxynaphthaline, 1,8-di-hydroxynaphthaline, 4-hydroxyindole, 6-hydroxyindole, 7-hydroxyindole, 4-hydroxyindoline, 6-hydroxyindoline, 7-hydroxyindoline or the physiologically acceptable salts of the abovementioned compounds.

Oxidation dye precursor of the developer type and of the coupler type are preferably used in certain combinations. In relation to the present invention, the following combinations have proven to be especially advantageous: p-toluylenediamine/resorcinol; p-toluylenediamine/2-methyl-resorcinol; p-toluylenediamine/5-amino-2-methylphenol; p-toluylenediamine/3-aminophenol; p-toluylenediamine 2-(2,4-diaminophenoxy)ethanol; p-toluylenediamine/1,3-bis(2,4-diaminophenoxy)propane; p-toluylenediamine/1-methoxy-2-amino-4-(2-hydroxyethylamino)benzene; p-toluylenediamine/2-amino-3-hydroxypyridine; p-toluylenediamine/1-naphthol; 2-(2-hydroxyethyl)-p-phenylenediamine/resorcinol; 2-(2-hydroxyethyl)-p-phenylenediamine/2-methylresorcinol; 2-(2-hydroxyethyl)-p-phenylenediamine/5-amino-2-methylphenol; 2-(2-hydroxyethyl)-p-phenylenediamine/3-aminophenol; 2-(2-hydroxyethyl)-p-phenylenediamine/2-(2,4-diaminophenoxy)ethanol; 2-(2-hydroxyethyl)-p-phenylenediamine/1,3-bis-(2,4-diaminophenoxy)propane; 2-(2-hydroxyethyl)-p-phenylenediamine/1-methoxy-2-amino-4-(2-hydroxyethylamino)benzene; 2-(2-hydroxy-ethyl)-p-phenylenediamine/2-amino-3-hydroxypyridine; 2-(2-hydroxyethyl)-p-phenylenediamine/1-naphthol; 2-methoxymethyl-p-phenylenediamine/resorcinol; 2-methoxymethyl-p-phenylenediamine/2-methylresorcinol; 2-methoxymethyl-p-phenylenediamine/5-amino-2-methyl-phenol; 2-methoxymethyl-p-phenylenediamine/3-aminophenol; 2-methoxymethyl-p-phenylenediamine/2-(2,4-di-aminophenoxy)ethanol; 2-methoxymethyl-p-phenylenediamine/1,3-bis(2,4-diaminophenoxy)propane; 2-methoxymethyl-p-phenylenediamine 1-methoxy-2-amino-4-(2-hydroxyethylamino)benzene; 2-methoxymethyl-p-phenylenediamine 2-amino-3-hydroxypyridine; 2-methoxymethyl-p-phenylenediamine/1-naphthol; N-(4-amino-3-methylphenyl)-N-[3-(1H-imidazole-1-yl)propyl]amine/resorcinol; N-(4-amino-3-methylphenyl)-N-[3-(1H-imidazole-1-yl)propyl]amine/2-methylresorcinol; N-(4-amino-3-methylphenyl)-N-[3-(1H-imidazole-1-yl)propyl]amine/5-amino-2-methylphenol; N-(4-amino-3-methylphenyl)-N-[3-(1H-imidazole-1-yl)propyl]amine/3-aminophenol; N-(4-amino-3-methylphenyl)-N-[3-(1H-imidazole-1-yl)propyl]amine/2-(2,4-diaminophenoxy) ethanol; N-(4-amino-3-methylphenyl)-N-[3-(1H-imidazole-1-yl)propyl]amine/1,3-bis(2,4-diaminophenoxy)-propane; N-(4-amino-3-methylphenyl)-N-[3-(1H-imidazole-1-yl) propyl]amine/1-methoxy-2-amino-4-(2-hydroxyethyl-amino)benzene; N-(4-amino-3-methylphenyl)-N-[3-(1H-imidazole-1-yl)propyl]amine/2-amino-3-hydroxypyridine; N-(4-amino-3-methylphenyl)-N-[3-(1H-imidazole-1-yl) propyl]amine/1-naphthol; 4,5-diamino-1-(2-hydroxyethyl) pyrazole/resorcinol; 4,5-diamino-1-(2-hydroxyethyl)pyrazole/2-methylresorcinol; 4,5-diamino-1-(2-hydroxyethyl) pyrazole/5-amino-2-methylphenol; 4,5-diamino-1-(2-hydroxyethyl)pyrazole/3-aminophenol; 4,5-diamino-1-(2-hydroxyethyl)pyrazole/2-(2,4-diamino-phenoxy)ethanol; 4,5-diamino-1-(2-hydroxyethyl)pyrazole/1,3-bis(2,4-di-aminophenoxy)propane; 4,5-diamino-1-(2-hydroxyethyl) pyrazole/1-methoxy-2-amino-4-(2-hydroxyethylamino)ben-zene; 4,5-di-amino-1-(2-hydroxyethyl)pyrazole/2-amino-3-hydroxypyridine; 4,5-diamino-1-(2-hydroxyethyl)pyrazole/ 1-naphthol. However, it is also possible in the context of the present invention to additionally use, besides the abovementioned combinations, other oxidation dye precursors in the composition (M2) used according to method step (d).

Especially appealing colorations are obtained if the composition (M2) used in method step (d) includes at least one developer component selected from the group of p-phenylenediamine, p-toluylenediamine, N,N-bis-(2-hydroxyethyl)amino-p-phenylenediamine, 1,3-bis-[(2-hydroxyethyl-4'-aminophenyl)amino]-propane-2-ol, 1,10-bis-(2',5'-diaminophenyl)-1,4,7,10-tetraoxadecane, 4-aminophenol, 4-amino-3-methylphenol, bis-(5-amino-2-hydroxyphenyl) methane, 2,4,5,6-tetraaminopyrimidine, 2-hydroxy-4,5,6-triaminopyrimidine, 4,5-diamino-1-(2-hydroxyethyl)-pyrazole, physiologically acceptable salts thereof and mixtures thereof, and at least one coupler component selected from the group of resorcinol, 2-methylresorcinol, 5-methylresorcinol, 2,5-dimethylresorcinol, 4-chlororesorcinol, resorcinol monomethyl ether, 5-aminophenol, 5-amino-2-methylphenol, 5-(2-hydroxyethyl)amino-2-methylphenol, 3-amino-4-chloro-2-methylphenol, 3-amino-2-chloro-6-methylphenol, 3-amino-2,4-dichlorophenol, 2,4-diaminophenoxyethanol, 2-amino-4-(2'-hydroxyethyl)amino-anisolsulfate, 1,3-bis-(2,4-diaminophenoxy)propane, 2-amino-3-hydroxypyridine, 2-methylamino-3-amino-6-methoxypyridine, 2,6-dihydroxy-3,4-dimethylpyridine, 3,5-diamino-2,6-dimethoxypyridine, 1-naphthol, 2-methyl-1-naphthol, 1,5-dihydroxynaphthaline, 2,7-dihydroxynaphthaline, 1-phenyl-3-methylpyrazole-5-on, 2,6-bis-[(2'-hydroxyethyl)amino]-toluene, 4-hydroxyindole, 6-hydroxyindole, 6-hydroxybenzomorpholine, and physiologically acceptable salts thereof and mixtures thereof.

Moreover, it is preferred in this context if the composition (M2) used in method step (d) includes at least one developer component selected from among p-toluylenediamine and physiologically acceptable salts thereof, and at least one coupler component selected from among resorcinol, 2-methylresorcinol, 2-amino-3-hydroxypyridine, 3-aminophenol, and physiologically acceptable salts thereof and mixtures thereof. When using the abovementioned oxidation dye precursors, especially good lightening or coloration is achieved which has a high level of resistance to environmental influences such as shampoos and UV light, sweat and friction.

In order to obtain balanced and subtle nuances, a provision can also be made in relation to the present invention that the composition (M2) used in method step (d) additionally includes at least one direct dye. Direct dyes are dyes which are applied directly to the hair without the need for any oxidative processes to produce the color. Direct dyes are usually nitro-phenylenediamines, nitro-aminophenols, azo dyes, anthraquinones, or indophenols.

Direct dyes can be categorized into anionic, cationic and nonionic direct dyes.

Preferred anionic direct dyes are the compounds known by the designations Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, and Tetrabromophenol Blue. Preferred cationic direct dyes are cationic triphenylmethane dyes such as Basic Blue 7, Basic Blue 26, Basic Violet 2, and Basic Violet 14, aromatic systems that are substituted with a quaternary nitrogen group, such as Basic Yellow 57, Basic Red 76, Basic Blue 99, Basic Brown 16, and Basic Brown 17, and HC Blue 16, as well as Basic Yellow 87, Basic Orange 31, and Basic Red 51. Preferred nonionic direct dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Furthermore, naturally occurring direct dyes such as those included in henna red, henna neutral, henna black, chamomile blossom, sandalwood, black tea, walnut, buckthorn bark, salvia, campeche wood, madder root, catechu and alkanet root.

Preferably, the composition (M2) used in method step (b) includes at least one direct dye in a total quantity of 0.001 to 10 wt %, preferably 0.01 to 8 wt %, more preferably 0.1 to 5 wt %, and particularly 0.5 to 3 wt % with respect to the total weight of the composition (M2).

The oxidation dye precursors (developers and couplers) themselves are not colored. The actual dyes are formed only as a result of the contacting of the oxidation dye precursors with an oxidizing agent (preferably hydrogen peroxide). In a chemical reaction, the developer components used as oxidation dye precursors (such as, for example, p-phenylenediamine derivatives or p-aminophenol derivatives) is first converted oxidatively using hydrogen peroxide into a reactive interstage, also called quinone imine or quinone diimine, which then reacts in an oxidative coupling reaction to form the respective dye.

The compositions (M2) additionally include one or more oxidizing agents that are different from atmospheric oxygen. Oxidizing agents that merit consideration are persulfates, peroxodisulfates, chlorites, hypochlorites and, in particular, hydrogen peroxide and/or one of its solid addition products to organic or inorganic compounds.

Methods that are preferred according to the invention are therefore characterized in that the composition (M2) used in method step (d) includes at least one oxidizing agent from the group of persulfates, chlorites, hydrogen peroxide, and addition products of hydrogen peroxide to urea, melamine, and sodium borate.

In the context of the present invention, it is advantageous if the aqueous composition (M2) used in method step (d) includes the at least one oxidizing agent in a total quantity of 1.0 to 12 wt %, preferably 1.5 to 12 wt %, more preferably 2.0 to 12 wt %, even more preferably 3.0 to 12 wt %, particularly 4.0 to 12 wt % with respect to the total weight of the composition (M2). For one, this quantity of oxidizing agent ensures sufficient setting of the reshaped keratinic fibers and ensures the reaction of the developer and coupler components used to the desired dyes. If hydrogen peroxide and solid addition products thereof are used, the above total quantity is calculated to 100% $H_2O_2$.

One especially preferred oxidizing agent in the context of the present invention is hydrogen peroxide. Methods that are preferred according to the invention are therefore characterized in that the composition (M2) used in method step (b) includes hydrogen peroxide as an oxidizing agent in a total quantity of 0.5 to 15 wt %, preferably 1 to 12.5 wt %, more preferably 1.5 to 10 wt %, and particularly 1.5 to 7.5 wt %, with respect to the total weight of the composition (M2). The abovementioned total quantity is calculated to 100% $H_2O_2$.

To achieve an intensified lightening and bleaching effect, the composition (M2) can also include at least one peroxo salt. Suitable peroxo salts are inorganic peroxo compounds, preferably selected from the group of ammonium peroxodisulfate, alkali metal peroxodisulfates, ammonium peroxomonosulfate, alkali metal peroxomonosulfates, alkali metal peroxodiphosphates, and alkaline earth metal peroxides, as well as mixtures thereof. Peroxodisulfates, particularly ammonium peroxodisulfate, potassium peroxodisulfate, and sodium peroxodisulfate, are especially preferred.

The abovementioned peroxo salts are included in a total quantity of 0.5 to 20 wt %, preferably 1 to 12.5 wt %, more preferably 2.5 to 10 wt %, particularly 3 to 6 wt % with respect to the total weight of the composition (M2).

The dyeing agent (M2) can also include at least one alkalizing agent to set a basic pH value. The setting of a basic pH value using the at least one alkalizing agent is necessary in order to ensure the opening of the outer cuticle and enable penetration of the oxidation dye precursors into the hair.

Methods that are preferred according to the invention are therefore characterized in that the composition (M2) used in method step (d) have a pH value from pH 7.0 to pH 14.0, preferably from pH 8.8 to pH 11.0, more preferably from pH 9.0 to pH 10.8, and particularly from pH 9.2 to pH 10.5 at a temperature of 20° C.

Organic alkalizing agents that can be used according to the invention are preferably selected from among alkanolamine from primary, secondary, or tertiary amines with a $C_2$-$C_5$ alkyl parent which bears at least one hydroxyl group. Alkanolamines that are very especially preferred according to the invention are selected from the group of 2-aminoethane-1-ol(monoethanolamine), 2-amino-2-methylpropane-1-ol, and 2-amino-2-methyl-propane-1,3-diol, as well as mixtures thereof. One particularly preferred alkanolamine is monoethanolamine. Suitable basic amino acids are lysine, arginine, and ornithine. Inorganic alkalizing agents according to the invention are preferably selected from the group of sodium hydroxide, potassium hydroxide, calcium hydroxide, barium hydroxide, sodium phosphate, potassium phosphate, sodium silicate, potassium silicate, sodium carbonate, and potassium carbonate, as well as mixtures thereof.

Special methods according to the invention are therefore characterized in that the composition (M2) used in method step (b) includes, as an alkalizing agent, at least one compound from the group of sodium hydroxide, potassium hydroxide, ammoniac, monoethanolamine, 2-amino-2-methyl propane, and alkali and ammonium hydrogen carbonates.

In this context, it is especially preferred if the composition (M2) used in method step (b) includes monoethanolamine as an alkalizing agent. This prevents the occurrence of unpleasant odors during oxidative coloration, particularly lightening or coloration.

To set a basic pH value, the alkalizing agents can be employed in certain quantities. It is preferred according to the invention if the composition (M2) used in method step (d) includes the at least one alkalizing agent in a total quantity of 0.1 to 15 wt %, preferably 0.5 to 12 wt %, more preferably 1.0 to 10 wt %, and particularly 2.0 to 6.0 wt % with respect to the total weight of the aqueous composition (M2).

The oxidative dyeing agent (M2) is also an aqueous composition that is present in the form of a foam. In order to ensure a stable foam, the composition (M2) therefore has at least one surfactant.

According to one embodiment of the present invention, the composition (M2) used in method step (d) includes, as a surfactant, at least one alkyl betaine, at least one alkyl polyglucoside, at least one nonionic surfactant, and at least one anionic surfactant. Particularly good wetting of the keratinic fibers is achieved through the mousse-type formulation. Particularly good wetting is necessary, since the keratinic fibers located on the styling aids are not freely accessible for the dyeing agent (M2), so there is a danger of an uneven coloring result in the event of insufficient wetting. Moreover, the application as a foam prevents the running-off of the dyeing agent (M2) during the removal of the styling aids.

In this context, it is preferred if the composition (M2) used in method step (d) includes, as surfactant, alkyl betaines of formula (II)

(II)

where $R^1$ and $R^3$, each independently of one another, stand for a $C_1$-$C_4$ alkyl group or a $C_2$-$C_4$ hydroxyalkyl group, particularly methyl group, and for $R^2$ stands for a saturated or unsaturated $C_{10}$-$C_{20}$ alkyl chain, particularly coco alkyl group. One especially preferred alkyl betaine of formula (II) is coco alkyldimethyl betaine, for example, which is commercially available under the trade name Genagen KB from Clariant.

Furthermore, it is preferred in the framework of this embodiment if the composition (M2) used in method step (d) includes, as surfactant, alkyl polyglucosides of formula (III)

(III), where $R^4$ stands for an alkyl and/or alkenyl residue with 4 to 22 carbon atoms, G stands for a sugar residue with 5 or 6 carbon atoms, and p stands for numbers from 1 to 10. The index number p in the general formula (III) indicates the degree of oligomerization (DP), i.e., the distribution of mono- and oligoglucosides, and stands for a number between 1 and 10. While p can be an integer in a given compound and can assume above all the values p=1 to 6 here, the value p is an analytically determined quantity identified for a specific alkyl oligoglucoside, which usually represents a fractional number. Alkyl and/or alkenyl oligoglucosides having a mean degree of oligomerization p from 1.1 to 3.0 are preferably used according to the invention. From an application engineering perspective, such alkyl and/or alkenyl oligoglucosides are preferred whose degree of oligomerization is less than 1.7 and particularly lies between 1.2 and 1.7. The alkyl or alkenyl residue $R^{14}$ can be derived from primary alcohols with 4 to 6, preferably 8 to 16 carbon atoms. Alkyl oligoglucosides based on hardened $C_{12/14}$ coco alcohol with a DP from 1-3, such as those which are commercially available under the INCI designation "coco glucoside," for example, are very especially preferred according to the invention.

In addition, it is preferred in the framework of this embodiment if the composition (M2) used in method step (d) includes, as surfactant, nonionic surfactants with an HLB value of greater than 10, particularly greater than 14, that have at least 30 ethylene oxide units. Suitable nonionic surfactants are, for example, addition products of 20 to 60 mol ethylene oxide to castor oil and hardened castor oil, particularly the compounds known by the INCI designations PEG-40 Hydrogenated Castor Oil and PEG-60 Hydrogenated Castor Oil.

The use of anionic surfactants is also possible in the context of this embodiment. These are characterized by a hydrophilic anionic group, such as a carboxylate, sulfate, sulfonate or phosphate group, for example, and a lipophilic alkyl group with about 8 to 30 carbon atoms. In addition, these surfactants can have glycol or polyglycol ether groups, ester, ether and amide groups, as well as hydroxyl groups. Anionic surfactants that are suitable according to the invention can be used in the form of the sodium, potassium, and ammonium salts as well as the mono-, di-, and trialkanol ammonium salts with 2 to 4 carbon atoms in the alkanol group. Preferably, the composition (M2) used in method step (d) includes, as surfactant, at least one anionic surfactant from the group of the alkyl polyglycol ether sulfates, alkyl sulfates, and/or sulfosuccinic acid monoalkylpolyoxyethyl esters with 8 to 18 carbon atoms in the alkyl group and 1 to 10, preferably 1 to 3 oxyethyl groups in the polyoxyethylene group.

Through the use of the abovementioned surfactant combination, both a large quantity of foam and a high level of foam stability can be achieved. The mousse-type texture of the composition (M2) results in uniform wetting of the keratinic fibers located on the styling aids, thereby preventing an uneven coloring result. Furthermore, the mousse-type composition (M2) can be distributed well on the keratinic fibers and does not run off during the exposure time.

In order to achieve a mousse-type texture of the composition (M2), the previously mentioned surfactants can be used in a certain quantity range. It is therefore preferred according to the invention if the composition (M2) used in method step (d) includes the at least one surfactant in a total quantity of 5.0 to 40 wt %, preferably 10 to 35 wt %, more preferably 15 to 30 wt %, and particularly 20 to 27 wt % with respect to the total weight of the aqueous composition (M2).

In the framework of another embodiment of the present invention, a provision can be made that the compositions (M1) and (M2) used in method steps (b), (d), and (f) each additionally include at least one other compound selected from the group of (i) thickeners; (ii) linear or branched, saturated or unsaturated alcohols with 8 to 20 carbon atoms; (iii) cationic polymers; (iv) extracts, particularly algae extracts; and (v) mixtures thereof.

In the context of this embodiment, thickeners have proven to be especially advantageous which include at least one monomer of the type of acrylic acid or methacrylic acid as well as derivatives thereof. One polymer that is very especially preferred according to the invention is a copolymer of two or more monomers selected from among acrylic acid, methacrylic acid, and esters thereof with $C_1$-$C_4$ alkyl groups. One polymer that is very especially preferred according to the invention is a copolymer known by the INCI designation Acrylates Copolymer comprising two or more monomers selected from among acrylic acid, methacrylic acid, and esters thereof with $C_1$-$C_4$ alkyl groups. Another polymer that is very especially preferred according to the invention is a crosslinked acrylic acid homopolymer, which is also referred to as a carbomer. Other polymers that are very especially preferred according to the invention are methacrylic acid-free copolymers of acrylic acid and acrylic acid $C_1$-$C_4$ esters.

The thickener is preferably used in compositions (M1) and/or (M2) in a total quantity of 0.05 to 2 wt %, particularly 0.1 to 1 wt %, with respect to the total weight of composition (M1) or (M2).

In the context of the present invention, it can be advantageous to also add at least one linear or branched, saturated or unsaturated alcohol to compositions (M1) and (M2). Alcohols with $C_8$-$C_{22}$, particularly with $C_{12}$-$C_{22}$ alkyl groups can be used as alcohols. Examples of alcohols that can be used in terms of the invention include decanol, octanol, octenol, dodecenol, decenol, octadienol, dodecadienol, decadienol, oleyl alcohol, eruca alcohol, ricinol alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol, and behenyl alcohol, as well as Guerbet alcohols thereof. The alcohols preferably originate from natural carboxylic acids, in which case it can usually be assumed that they are obtained from the esters of the carboxylic acids through reduction. Alcohol cuts can also be used according to the invention which are produced through reduction of naturally occurring triglycerides such as beef tallow, palm oil, peanut oil, rapeseed oil, cottonseed oil, soy oil, sunflower oil, and linseed oil, or from the transesterification products thereof carboxylic acid esters produced with corresponding alcohols, and therefore represent a mixture of different alcohols. Such substances are commercially available under the designations Stenol®, e.g., Stenol® 1618 or Lanette®, e.g. Lanette® O or Lorol®, e.g., Lorol® CS, Lorol® C14, Lorol® C18, Lorol® CS-18, HD-Ocenol®, Crodacol®, e.g. Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16, or Isocarb®, for example.

The alcohols can be included in compositions (M1) and/or (M2) in a total quantity of 0.1 to 20 wt %, particularly 0.1 to 10 wt %, with respect to the total weight of composition (M1) or (M2).

The compositions (M1) and/or (M2) can also include at least one cationic polymer. Cationic polymers are to be understood as polymers having groups in the main and/or side chain that can be "temporarily" or "permanently" cationic. According to the invention, those polymers are referred to as being "permanently cationic" which have a cationic group independently of the pH value of the agent. As a rule, these are polymers containing a quaternary nitrogen atom, for example in the form of an ammonium group. Preferred cationic groups are quaternary ammonium groups. Particularly such polymers in which the quaternary ammonium group is bonded via a $C_{14}$ hydrocarbon group to a main polymer chain constructed from acrylic acid, methacrylic acid, or derivatives thereof have proven to be especially suitable.

Especially preferred cationic polymers are selected from among the compounds with the INCI designation "Polyquaternium." Polyquaternium-2, Polyquaternium-4, Polyquaternium-5, Polyquaternium-6, Polyquaternium-7, Polyquaternium-10, Polyquaternium-11, Polyquaternium-17, Polyquaternium-18, Polyquaternium-22, Polyquaternium-27, Polyquaternium-37, and Polyquaternium-39 are especially preferably used; Polyquaternium-22, Polyquaternium-37, and Polyquaternium-39 are extraordinarily preferred, and Polyquaternium-22 is most preferred.

Examples of other preferred cationic polymers are
  quaternized cellulose derivatives such as those which are commercially available under the names Celquat® and Polymer JR®. The compounds Celquat® H 100, Celquat® L 200, and Polymer JR®400 are preferred quaternized cellulose derivatives,
  cationized honey, such as the commercial product Honeyquat® 50,
  cationic guar derivatives, such as, in particular, the products sold under the trade names Cosmedia®Guar and Jaguar®,
  polysiloxanes with quaternary groups, such as the commercially available products 02-7224 (manufacturer: Dow Corning; a stabilized trimethylsilylamodimethicone), Dow Corning® 929 Emulsion (containing a hydroxyl amino-modified silicone, which is also referred to as amodimethicone), SM-2059 (manufacturer: General Electric), SLM-55067 (manufacturer:

Wacker), and Abil®-Quat 3270 and 3272 (manufacturer: Th. Goldschmidt; diquaternary polydimethylsiloxane, Quaternium-80), polymeric dimethyldiallylammonium salts and copolymers thereof with esters and amides of acrylic acid and methacrylic acid. The products available commercially under the names Merquat®100 (poly(dimethyldiallylammonium chloride)) and Merquat®550 (dimethyldiallylammonium chloride acrylamide copolymer) are examples of such cationic polymers, copolymers of vinyl pyrrolidone with quaternized derivatives of dialkylamino alkyl acrylate and methacrylate, such as vinyl pyrrolidone dimethylaminoethylmethacrylate copolymers quaternized with diethyl sulfate, for example. Such compounds are commercially available under the names Gafquat®734 and Gafquat®755, vinyl pyrrolidone vinylimidazolium methochloride copolymers, such as those sold under the names Luviquat® FC 370, FC 550, FC 905, and HM 552, quaternized polyvinyl alcohol.

The copolymers of vinyl pyrrolidone such as those which are available as the commercial products Copolymer 845 (manufacturer: ISP), Gaffix® VC 713 (manufacturer: ISP), Gafquat®ASCP 1011, Gafquat®HS 110, Luviquat®8155, and Luviquat® MS 370 can also be used according to the invention.

The cationic polymers can be included in compositions (M1) and/or (M2) in a total quantity of 0.1 to 5.0 wt %, particularly 0.25 to 3.0 wt %, with respect to the total weight of composition (M1) or (M2).

Finally, the compositions (M1) and/or (M2) can also include at least one extract, particularly an algae extract. Algae extracts include components such as carotinoids, proteins and amino acids, polyphenols, unsaturated fatty acids and vitamins, polysaccharides, antioxidant minerals such as selenium and zinc, antioxidant enzymes such as catalase, superoxide dismutase and peroxidase, as well as minerals such as potassium, magnesium, and iron. Algae extracts that are especially preferably used are aqueous or aqueous-alcoholic extracts from the blue algae taxon spirulina. Such extracts can be obtained, for example, by extracting blue algae with water or a water/glycol mixture.

The extracts can be included in compositions (M1) and/or (M2) in a total quantity of 0.0001 to 1 wt %, preferably 0.001 to 0.5 wt %, and particularly 0.005 to 0.1 wt %, with respect to the total weight of composition (M1) or (M2).

The present invention is delineated particularly by the following points:

1. A method for permanently reshaping and changing the color of keratinic fibers, particularly human hairs, in a single process, with the method comprising the following method steps in the indicated sequence:
a) styling of keratinic fibers using styling aids,
b) application of an aqueous composition (M1) including at least one keratin-reducing compound, at least one alkalizing agent, and at least one surfactant, from an applicator as a foam onto the keratinic fibers located on the styling aids and leaving this composition (M1) on the keratinic fibers located on the styling aids for a period of 5 to 50 minutes,
c) rinsing and, optionally, drying of the keratinic fibers located on the styling aids,
d) application of a composition (M2) including at least one oxidation dye precursor, at least one oxidizing agent, at least one alkalizing agent, and at least one surfactant, from an applicator as a foam onto the keratinic fibers located on the styling aids and leaving this composition (M2) on the keratinic fibers located on the styling aids for a period of 10 to 15 minutes,
e) removal of the styling aids from the keratinic fibers,
f) distribution of the composition applied in step (d) to the keratinic fibers and/or repeated application of the composition (M2) including at least one oxidation dye precursor, at least one oxidizing agent, at least one alkalizing agent, and at least one surfactant, from an applicator as a foam onto the keratinic fibers and leaving this composition (M2) on the keratinic fibers located on the styling aids for a period of 15 to 30 minutes,
g) rinsing of the keratinic fibers, and
h) optionally, application of a post-treatment agent to the keratinic fibers.

2. The method according to point 1, characterized in that a permanent wave is performed as a permanent reshaping and lightening or coloration is performed as a color change.

3. The method according to any one of points 1 or 2, characterized in that the styling aids used in method step (a) have a diameter from 1 to 10 cm, preferably from 1 to 8 cm, more preferably from 1 to 6 cm, particularly from 2 to 5 cm.

4. The method according to any one of the preceding points, characterized in that the composition (M1) used in method step (b) includes at least one keratin-reducing compound in a total quantity of 5 to 20 wt %, preferably 7 to 18 wt %, more preferably 9 to 16 wt %, and particularly 10 to 15 wt % with respect to the total weight of the aqueous composition (M1).

5. The method according to any one of the preceding points, characterized in that the composition (M1) used in method step (b) includes, as an alkalizing agent, at least one compound from the group of sodium hydroxide, potassium hydroxide, ammonium hydroxide, ammoniac, monoethanolamine, 2-amino-2-methyl propane, and alkali and ammonium hydrogen carbonates.

6. The method according to any one of the preceding points, characterized in that the composition (M1) used in method step (b) includes at least one alkalizing agent in a total quantity of 0.1 to 15 wt %, preferably 0.5 to 12 wt %, more preferably 1.0 to 10 wt %, and particularly 1.5 to 7 wt % with respect to the total weight of the aqueous composition (M1).

7. The method according to any one of the preceding points, characterized in that the composition (M1) used in method step (b) has a weight ratio of the keratin-reducing compound to the alkalizing agent from 1:200 to 1:1, preferably from 1:50 to 1:1, more preferably from 1:30 to 1:1, even more preferably from 1:20 to 1:1, and particularly from 1:10 to 1:1.

8. The method according to any one of the preceding points, characterized in that the composition (M1) used in method step (b) includes, as a surfactant, at least one compound from the group of alkyl (ether) sulfates, alkyl betaines, alkyl polyglucosides, and nonionic surfactants.

9. The method according to any one of the preceding points, characterized in that the composition (M1) used in method step (b) includes at least one surfactant in a total quantity of 1.0 to 20 wt %, preferably 2.0 to 15 wt %, more preferably 2.5 to 10 wt %, and particularly 3.0 to 7.0 wt % with respect to the total weight of the aqueous composition (M1).

10. The method according to any one of the preceding points, characterized in that the composition (M2) used in method step (d) includes at least one oxidation dye precursor in a total quantity of 0.001 to 10 wt %, preferably 0.01 to 8 wt %, more preferably 0.1 to 5 wt %, and particularly 0.5 to 3 wt % with respect to the total weight of the composition (M2).

11. The method according to any one of the preceding points, characterized in that the composition (M2) used in method step (b) includes hydrogen peroxide as an oxidizing agent in a total quantity of 0.5 to 15 wt %, preferably 1 to 12.5 wt %, more preferably 1.5 to 10 wt %, and particularly 1.5 to 7.5 wt %, with respect to the total weight of the composition (M2).

12. The method according to any one of the preceding points, characterized in that the composition (M2) used in method step (d) includes, as an alkalizing agent, at least one compound from the group of sodium hydroxide, potassium hydroxide, ammoniac, monoethanolamine, 2-amino-2-methyl propane, and alkali and ammonium hydrogen carbonates.

13. The method according to any one of the preceding points, characterized in that the composition (M2) used in method step (d) includes at least one the alkalizing agent in a total quantity of 0.1 to 15 wt %, preferably 0.5 to 12 wt %, more preferably 1.0 to 10 wt %, and particularly 2.0 to 6.0 wt % with respect to the total weight of the aqueous composition (M2).

14. The method according to any one of the preceding points, characterized in that the composition (M2) used in method step (d) includes, as a surfactant, at least one alkyl betaine, at least one alkyl polyglucoside, at least one non-ionic surfactant, and at least one anionic surfactant.

15. The method according to any one of the preceding points, characterized in that the composition (M2) used in method step (d) includes at least one surfactant in a total quantity of 5.0 to 40 wt %, preferably 10 to 35 wt %, more preferably 15 to 30 wt %, and particularly 20 to 27 wt % with respect to the total weight of the aqueous composition (M2).

The following examples are intended to elucidate preferred embodiments of the invention without limiting them.

EXAMPLES

1. Aqueous Composition (M1)—Waving Agent

The aqueous composition (M1) in the form of a waving agent was obtained by mixing the components listed below.

TABLE 1

Waving agent

| Raw material | Quantity (wt %) |
| --- | --- |
| Ammonium thioglycolate (71% aqueous | 12.5 |
| EDTA disodium salt | 0.2 |
| Ammoniac (25% aqueous solution) | 1.8 |
| Ammonium bicarbonate | 2.5 |
| Cremophor CO 60 [1] | 1.0 |
| Texapon NSO [2] | 3.0 |
| Eumulgin L [3] | 1.5 |
| Perfume | 0.5 |
| Water | Up to 100 |

[1] Cremophor CO 60 (INCI designation: PEG-60 Hydrogenated Castor Oil; BASF)
[2] Texapon NSO (INCI designation: Sodium laureth sulfate; BASF)
[3] Eumulgin L (INCI designation: PPG-1-PEG-9 lauryl glycol ether; BASF)

2. Oxidative Dyeing Agent (M2)

The coloring cream of table 2 described below was prepared and mixed with the oxidizing agent preparation O1 in a ratio of 1:1 immediately prior to application in each case:

TABLE 2

Coloring cream

| Raw material | Quantity (wt %) |
| --- | --- |
| Plantacare 818 UP [1] | 25 |
| Genagen KB [2] | 30 |
| Cremophor CO 60 [3] | 3.0 |
| EDTA, tetrasodium salt | 0.2 |
| Monoethanolamine | 6.0 |
| Sodium sulfite | 0.2 |
| Vitamin C | 0.05 |
| L-serine | 1.0 |
| Eau Vitale d'algue bleue [4] | 2.0 |
| Merquat 281 [5] | 3.0 |
| p-toluylenediamine sulfate | 1.6 |
| Resorcinol | 0.4 |
| 2-methylresorcinol | 0.4 |
| 3-aminophenol | 0.05 |
| 2-amino-3-hydroxypyridine | 0.03 |
| Perfume | 0.5 |
| Water | Up to 100.0 |

[1] Plantacare 818 UP (INCI designation: Coco-Glucoside, Aqua (Water); Cognis)
[2] Genagen KB (INCI designation: Coca-Betaine; Clariant)
[3] Cremophor CO 60 (INCI designation: PEG-60 Hydrogenated Castor Oil; BASF)
[4] Eau Vitale d'algue bleue (INCI designation: Aqua (Water), Plankton Extract; Penoxyethanol; Soliance)
[5] Merquat 281 (INCI designation: Polyquaternium-22; Lubrizol)

TABLE 3

Oxidizing agent preparation O1

| Raw material | Wt % |
| --- | --- |
| Dipicolinic acid | 0.1 |
| 50% NaOH | 0.7 |
| Disodium pyrophosphate | 0.03 |
| Hydroxyethane diphosphonic acid | 1.5 |
| Texapon NSO UP [1] | 2.0 |
| Aculyn 33 A [2] | 2.5 |
| Hydrogen peroxide, 50% | 15 |
| Water | Up to 100.0 |

[1] Texapon NSO UP (INCI designation: Sodium laureth sulfate; BASF)
[2] Aculyn 33 A (INCI designation: Acrylates Copolymer; Rahm & Haas)

3. Experimental Procedure and Assessment of the Results:

Undamaged hair was moistened with water and rubbed down with a hand towel. A strand of hair was severed in the width of the curler used and combed smooth. The strand of hair was placed in the middle between a sheet of folded perm paper and wound onto curlers having a diameter of 2 to 5 cm each with holes (about 500 to 6,000 holes per curler). This process was repeated until all of the hairs were wound on curlers.

The foam-type waving agent prepared according to point 1 was applied to the wound hair and left on the hair for an exposure time of 20 to 40 minutes. The wound hair was then rinsed out with water having a temperature of 30° C. and dried slightly using a hairdryer.

After the slight drying, the foam-type oxidative dyeing agent prepared according to point 2 was applied to the wound hair and left on the hair for an exposure time of 10 to 15 minutes. The perm curlers were then removed, and the remaining foam was distributed in the hair. After an additional exposure time of 15 to 30 minutes, the hair was rinsed out with water having a temperature of 30° C., rubbed down with a hand towel, and dried with a hairdryer.

A uniform waving and coloring result resulted, and the hair was damaged only very slightly by the method according to the invention or not at all.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for permanently reshaping and changing the color of keratinic fibers, in a single process, with the method comprising the following method steps in the indicated sequence:
    a) styling of keratinic fibers using styling aids,
    b) application of an aqueous composition (M1) including at least one keratin-reducing compound selected from the group consisting of thioglycolic acid, thiolactic acid, cysteine, and salts thereof and present in a total quantity of 10 to 15 wt % based on the total weight of the aqueous composition (M1), at least one alkalizing agent that is ammonium hydrogen carbonate and/or ammonium hydroxide, and present in a total quantity of 1.5 to 7 wt % based on the total weight of the aqueous composition (M1), and at least one surfactant selected from the group consisting of alkyl (ether) sulfates, alkyl betaines, alkyl polyglucosides, and nonionic surfactants, and present in a total quantity of 3.0 to 7.0 wt % based on the total weight of the aqueous composition (M1), from an applicator as a foam onto the keratinic fibers located on the styling aids and leaving this aqueous composition (M1) on the keratinic fibers located on the styling aids for a period of 5 to 50 minutes,
    c) rinsing and, optionally, drying of the keratinic fibers located on the styling aids,
    d) application of an aqueous foam composition (M2) including at least one oxidation dye precursor present in an amount of from 0.5 to 3 wt % with respect to the total weight of the aqueous foam composition (M2), at least one oxidizing agent that is hydrogen peroxide and is present in a total quantity of 1.5 to 7.5 wt % based on the total weight of the aqueous foam composition (M2), at least one alkalizing agent that is monoethanolamine and that is present in an amount of from 2.0 to 6.0 wt % with respect to the total weight of the aqueous foam composition (M2), and at least one surfactant from an applicator onto the keratinic fibers located on the styling aids and leaving this aqueous foam composition (M2) on the keratinic fibers located on the styling aids for a period of 10 to 15 minutes,
    e) removal of the styling aids from the keratinic fibers,
    f) distribution of the aqueous foam composition (M2) applied in step (d) remaining on the keratinic fibers and/or repeated application of the aqueous foam composition (M2) and leaving this aqueous foam composition (M2) on the keratinic fibers for a period of 15 to 30 minutes,
    g) rinsing of the keratinic fibers, and
    h) optionally, application of a post-treatment agent to the keratinic fibers
        wherein the aqueous foam composition (M2) used in step (d) includes, as a surfactant, at least one alkyl betaine, at least one alkyl polyglucoside, at least one nonionic surfactant having an HLB value of greater than 10, and at least one anionic surfactant,
        wherein the aqueous foam composition (M2) used in method step (d) includes the at least one surfactant in total quantity of 20 to 27 wt % with respect to the total weight of the aqueous foam composition (M2), and
        wherein each foam of step (b) and (d) is independently a colloid-chemical system composed of gas-filled cells that are bordered by a fluid, semifluid, or highly viscous cell web.

2. The method as set forth in claim 1, wherein the aqueous composition (M1) used in method step (b) has a weight ratio of the keratin-reducing compound to the alkalizing agent from 1:200 to 1:1.

3. The method as set forth in claim 1, wherein the aqueous composition (M1) used in method step (b) has a weight ratio of keratin-reducing compound to alkalizing agent of 1:10 to 1:1.

4. The method as set forth in claim 1, wherein the aqueous composition (M1) used in method step (b) has a weight ratio of keratin-reducing compound to alkalizing agent of 1:30 to 1:1.

* * * * *